US005874064A

United States Patent [19]
Edwards et al.

[11] Patent Number: 5,874,064

[45] **Date of Patent: *Feb. 23, 1999**

[54] AERODYNAMICALLY LIGHT PARTICLES FOR PULMONARY DRUG DELIVERY

[75] Inventors: David A. Edwards, State College, Pa.; Giovanni Caponetti, Piacenza, Italy; Jeffrey S. Hrkach, Somerville, Mass.; Noah Lotan, Haifa, Israel; Justin Hanes, Baltimore, Md.; Abdell Aziz Ben-Jebria, State College, Pa.; Robert S. Langer, Newton, Mass.

[73] Assignees: Massachusetts Institute of Technology, Cambridge, Mass.; The Penn State Research Foundation, University Park, Pa.

[ * ] Notice: The term of this patent shall not extend beyond the expiration date of Pat. No. 5,855,913.

[21] Appl. No.: 739,308

[22] Filed: Oct. 29, 1996

Related U.S. Application Data

[63] Continuation-in-part of Ser. No. 655,570, May 24, 1996.

[51] Int. Cl.[6] ..................... A61K 9/12

[52] U.S. Cl. ..................... 424/46; 424/45

[58] Field of Search ..................... 424/45, 46

[56] References Cited

U.S. PATENT DOCUMENTS

| | | |
|---|---|---|
| 4,161,516 | 7/1979 | Bell . |
| 4,272,398 | 6/1981 | Jaffe . |
| 4,590,206 | 5/1986 | Forrester et al. . |
| 4,741,872 | 5/1988 | De Luca et al. . |
| 4,818,542 | 4/1989 | De Luca et al. . |

(List continued on next page.)

FOREIGN PATENT DOCUMENTS

| | | |
|---|---|---|
| 0 072 046 A | 2/1983 | European Pat. Off. . |
| 0 257 915 | 3/1988 | European Pat. Off. . |
| 0 335 133 | 10/1989 | European Pat. Off. . |
| 91/04732 | 4/1991 | WIPO . |
| 94/07514 | 4/1994 | WIPO . |
| 95/00127 | 1/1995 | WIPO . |
| 95/07072 | 3/1995 | WIPO . |
| 95/24183 | 9/1995 | WIPO . |
| 96/09814 | 4/1996 | WIPO . |

OTHER PUBLICATIONS

Colthorpe et al., "The Pharmacokinetics of Pulmonary–Delivered Insulin: A Comparison of Intratracheals and Aerosol Administration to the Rabbit," *Pharm. Res.* 9:764 (1992).

Daly et al., "The Preparation of N–Carboxyanhydrides of α–Amino Acids Using Bis(Tricholoromethyl)Carbonate," *Tetrahedron Lett.*, 29:5859 (1988).

(List continued on next page.)

*Primary Examiner*—Raj Bawa
*Attorney, Agent, or Firm*—Arnall Golden & Gregory, LLP

[57] ABSTRACT

Improved aerodynamically light particles for drug delivery to the pulmonary system, and methods for their synthesis and administration are provided. In a preferred embodiment, the aerodynamically light particles are made of a biodegradable material and have a tap density less than 0.4 g/$cm^3$ and a mass mean diameter between 5 $\mu$m and 30 $\mu$m. The particles may be formed of biodegradable materials such as biodegradable polymers. For example, the particles may be formed of a functionalized polyester graft copolymer consisting of a linear α-hydroxy-acid polyester backbone having at least one amino acid group incorporated therein and at least one poly(amino acid) side chain extending from an amino acid group in the polyester backbone. In one embodiment, aerodynamically light particles having a large mean diameter, for example greater than 5 $\mu$m, can be used for enhanced delivery of a therapeutic agent to the alveolar region of the lung. The aerodynamically light particles incorporating a therapeutic agent may be effectively aerosolized for administration to the respiratory tract to permit systemic or local delivery of wide variety of therapeutic agents.

28 Claims, 2 Drawing Sheets

U.S. PATENT DOCUMENTS

| | | |
|---|---|---|
| 4,855,144 | 8/1989 | Leong et al. . |
| 4,857,311 | 8/1989 | Domb et al. . |
| 4,865,789 | 9/1989 | Castro et al. . |
| 4,904,479 | 2/1990 | Illum . |
| 5,069,936 | 12/1991 | Yen . |
| 5,160,745 | 11/1992 | De Luca et al. . |
| 5,169,871 | 12/1992 | Hughes et al. . |
| 5,384,133 | 1/1995 | Boyes et al. . |
| 5,456,917 | 10/1995 | Wise et al. . |
| 5,607,695 | 3/1997 | Ek et al. . |
| 5,612,053 | 3/1997 | Baichwal et al. . |

OTHER PUBLICATIONS

Damms and Bains, "The Cost of Delivering Drugs without Needles,", *J. Controlled Release*, 8–11 (1996).

Davies et al., "Breathing of half–micron aerosols. I. Experimental.," *J. Appl. Physiol.* 32:591–600 (1972).

Dorries and Valberg, "Heterogeneity of phagocytosis for inhaled versus instilled material," *Am. Rev. Resp. Disease*, 146: 831–837 (1991).

**Doubrow, Ed., "Microcapsules and Nanoparticles in Medicine and Pharmacy," CRC Press, Boca Raton, 1992.

Edwards, "The macrotransport of aerosol particles in the lung: Aerosol deposition phenomena," *J. Aerosol Sci.*, 26: 293–317 (1995).

Eldridge et al., "Biodegradable microspheres as a vaccine delivery system," *Mol. Immunol.*, 28:287–294 (1991).

Findeisen, "Uber das Absetzen kleiner in der Luft suspendierter Teilchen in der menshlichen Lunge bei der Atmung," *Pflugers Arch. D. Ges. Physiol.* 236:367–379 (1935).

French, Edwards, and Niven, "The influence of formulation on emission, deaggregation and deposition of dry powders for inhalation," *J. Aerosol Sci.*, 27: 769–783 (1996).

Ganderton, "The generation of respirable clouds from coarse powder aggregates," *J. Biopharmaceutical Sciences*, 3:101–105 (1992).

Gehr et al., "Surfactant and inhaled particles in the conducting airways: Structural, stereological, and biophysical aspects," *Microscopy Res. and Tech.*, 26: 423–436 (1993).

Gerrity et al., "Calculated deposition of inhaled particles in the airway generations of normal subjects," *J. Appl. Phys.*, 47:867–873 (1979).

Gonda, "Aerosols for delivery of therapeutic and diagnostic agents to the respiratory tract," in *Critical Reviews in Therapeutic Drug Carrier Systems* 6:273–313 (1990).

Gonda, "Preface. Major issues and future prospects in the delivery of therapeutic and diagnostic agents to the respiratory tract," *Adv. Drug Del. Rev.*, 5: 1–9 (1990).

Gonda, "Physico–chemical principles in aerosol delivery," in Topics in Pharmaceutical Sciences 1991, Crommelin, D.J. and K.K. Midha, Eds., Medpharm Scientific Publishers, Stuttgart, pp. 95–117, 1992.

Gonda, "Targeting by deposition," in *Pharmaceutical Inhalation Aerosol Technology* (ed. A.J. Hickey), Marcel Dekkar Inc., New York, 1992.

Heyder et al., "Mathematical models of particle deposition in the human respiratory tract," *J. Aerosol Sci.*, 17: 811–825 (1986).

Heyder and Rudolf, "Mathematical models of particle deposition in the human respiratory tract," *J. Aerosol Sci.*, 15:697–707 (1984).

Heyder et al., "Total Deposition of Aerosol Particles in the Human Respiratory Tract for Nose and Mouth Breathing," *J. Aerosol Sci.*, 6:311–328 (1975).

Hickey et al., "Use of particle morphology to influence the delivery of drugs from dry powder aerosols," *J. Biopharmaceutical Sci.*, 2(1/2):107–113 (1992).

Hirano et al, "Pulmonary clearance and Toxicity of Zinc Oxide Instilled into the Rat Lung," *Toxicology* 63:336–342 (1989).

Adjei and Garren, "Pulmonary Delivery of Peptide Drugs: Effect of Particle Size on Bioavailability of Leuprolide Acetate in Healthy Male Volunteers," *J. Pharm. Res.*, 7: 565–569 (1990).

Altschuler et al., "Aerosol deposition in the human respiratory tract," *Am. Med. Assoc. Arch. Indust. Health* 15:293–303 (1957).

Anderson et al., "Effect of Cystic Fibrosis on Inhaled Aerosol Boluses," *Am. Rev. Respir. Dis.*, 140: 1317–1324 (1989).

Barrera et al., "Synthesis and RGD Peptide Modification of a New Biodegradable Copolymer: Poly(lactic acid–co–l-ysine)," *J. Am. Chem. Soc.*, 115:11010 (1993).

Benita et al., "Characterization of drug–loaded poly(d,l–lactide) microspheres," *J. Pharm. Sci.* 73, 1721–1724 (1984).

Blackett and Buckton, "A Microcalorimetric Investigation of the Interaction of Surfactants with Crystalline and Partially Crystalline Salbutamol Sulphate in a Model Inhalation Aerosol System," *Pharmaceutical Research* 12(11):1689–1693 (1995).

Byron, "Determinants of drug and polypeptide bioavailability from aerosols delivered to the lung," *Adv. Drug. Del. Rev.*, 5: 107–132 (1990).

Clark and Egan, "Modeling the deposition of inhaled powdered drug aerosols," *J. Aerosol Sci.*, 25:175–186 (1994).

Clay et al., "Effect of aerosol particle size on bronchodilation with nebulized terbutaline in asthmatic subjects," *Thorax* 41:364–368 (1986).

Cohen et al., "Controlled Delivery Systems for Proteins Based on Poly(Lactic/Glycolic Acid) Micropheres," *Pharm. Res.*, 8(6): 713–720 (1991).

Hrkach et al., "Synthesis of Poly(L–lactic acid–co–L–l-ysine) graft copolymers," *Macromolecules*, 28:4736–4739 (1995).

Hrkach et al., "Poly(L–Lactic acid–co–amino acid) Graft Copolymers: A Class of Functional Biodegradable Biomaterials" in Hydrogels and Biodegradable Polymers for Bioapplications, ACS Symposium Series No. 627, Raphael M. Ottenbrite et al., Eds., American Chemical Society, Chapter 8, pp. 93–101, 1996.

Illum, "Microspheres as a Potential Controlled Release Nasal Drug Delivery System," *Delivery Systems for Peptide Drugs*, NY: Plenum, 1986.

Johnson et al., "Delivery of Albuterol and Ipratropiumbromide from Two Nebulizer Systems in Chronic Stable Asthma," *Chest*, 96, 6–10, 1989.

Kassem and Ganderton, "The Influence of Carrier Surface on the Characteristics of Inspirable Powder Aerosols," *J. Pharm. Pharmacol.*, 42:11 (1990).

Kawaguchi et al., "Phagocytosis of latex particles by leukocytes. I. Dependence of phagocytosis on the size and surface potential of particles," *Biomaterials* 7: 61–66 (1986).

Kobayashi et al., "Pulmonary Delivery of Salmon Calcitonin Dry Powders Containing Absorption Enhances in Rats," *Pharm. Res.*, 13(1): 80–83 (1996).

Komada et al., "Intratracheal Delivery of Peptide and Protein Agents: Absorption from Solution and Dry Powder by Rat Lung," *J. Pharm. Sci.* 83(6):863–867 (Jun., 1994).

Krenis and Strauss, "Effect of Size and Concentration of Latex Particles on Respiration of Human Blood Leucocytes," *Proc. Soc. Exp. Med.*, 107:748–750 (1961).

Lai et al., "Sustained bronchodilation with isoproterenol poly(glycolide–co–lactide) microspheres," *Pharm. Res.*, 10(1) 119–125 (1993).

Landahl, "On the removal of air–borne droplets by the human respiratory tract: I. The lung," *Bull. Math. Biophys.*, 12:43–56 (1950).
Langer,"New Methods of Drug Delivery," *Science*, 249:1527–1533 (1990).
LeCorre et al., Preparation and characterization of bupivacaine–loaded polylactide and polylactide–co–glycolide microspheres, *Int. J. Pharmaceutics*, 107:41–49 (1994).
Leone–Bay et al., "Microsphere formation in a series of derivatized α–amino acids: Properties, molecular modeling and oral delivery of salmon calcitonin," *J. Med. Chem.*, 38:4257–4262 (1995).
Liu et al., "Pulmonary Delivery of Free and Liposomal Insulin," *Pharm. Res.* 10(2):228–232 (1993).
Liu et al., "Moisture–induced aggregation of lyophilized proteins in the solid state," *Biotechnol. Bioeng.*, 37: 177–184 (1991).
Martonen, "Mathematical model for the selective deposition of inhaled pharmaceuticals," *J. Pharm. Sci.*, 82(12):1191–1198 (1993).
Masinde and Hickey, "Aerosolized aqueous suspensions of poly(L–lactic acid) microspheres," *Int. J. Pharmaceutics*, 100:123–131 (1993).
Mathiowitz et al., "Novel microcapsules for delivery systems," *Reactive Polymers* 6, 275–283 (1987).
Mathiowitz et al., "Polyanhydride microspheres. IV. Morphology and characterization of systems made by spray drying," *J. Appl. Polymer Sci.* 45, 125–134 (1992).
Mathiowitz et al., "Morphology of polyanhydride microsphere delivery systems," *Scanning Microscopy* 4: 329–340 (1990).
Mathiowitz and Langer, "Polyanhydride Microspheres as Drug Carriers I. Hot–Melt Microencapsulation," *J. Controlled Release* 5,13–22 (1987).
Mathiowitz et al., "Polyanhydrided microshperes as drug carriers. II. Microencapsulation by solvent removal," *J. Appl. Polymer Sci.* 35, 755–774 (1988).
Moren, "Aerosol dosage forms and formulations," in: *Aerosols in Medicine. Principles, Diagnosis and Therapy*, Moren, et al., Eds, Elsevier, Amsterdam, 1985.
Morimoto and Adachi, "Pulmonary Uptake of Liposomal Phosphatidylcholine Upon Intratracheal Administration to Rats," *Chem. Pharm. Bull.* 30(6):2248–2251 (1982).
Mulligan, "The Basic Science of Gene Therapy," *Science*, 260: 926–932 (1993).
Mumenthaier et al., "Feasibility Study on Spray–Drying Protein Pharmaceuticals: Recombinant Human Growth Hormone and Tissue–Type Plasminogen Activator," *Pharm. Res.*, 11: 12–20 (1994).
Niven et al., "The Pulmonary Absorption of Aerosolized and Intratracheally Instilled rhG–CSF and monoPEGylated rhG–CSF," *Pharm. Res.*, 12(9): 1343–1349 (1995).
Okumura et al, "Intratracheal delivery of insulin. Absorption from solution and aerosol by rat lung," *Int. J. Pharmaceutics*, 88:63–73 (1992).
Patton and Platz, "(D) Routes of Delivery: Case Studies (2) Pulomonary delivery of peptides and proteins," *Adv. Drug Del. Rev.*, 8: 179–196 (1992).
Patton et al., "Bioavailability of pulmonary delivered peptides and proteins: α–interferon, calcitonins and parathyroid hormones," *J. Controlled Release*, 28: 79–85 (1994).
**Pavia, "Lung Mucociliary Clearance," in Aerosols and the Lung: Clinical and Experimental Aspects, Clarke, S.W. and Pavia, D., Eds., Butterworths, London, 1984.
**Phalen, *Inhalation Studies: Foundations and Techniques.* CRC Press (Boca Rotan, Fl), 1984.
Pinkerton et al., "Aerosolized fluorescent microspheres detected in the lung using confocal scanning laser microscopy," *Microscopy Res. and Techn.*, 26:437–443 (1993).
Rudt and Muller, "In vitro Phagocytosis Assay of Nano– and Microparticles by chemiluminiscence. I. Effect of Analytical Parameters, Particle Size and Particle Concentration," *J. Contr. Rel.*, 22: 263–272 (1992).
Rudt et al., "In vitro phagocytosis assay of nano– and microparticles by chemiluminescence. IV. Effect of surface modification by coating of particles with poloxamine and Antarox CO on the phagocytic uptake," *J. Contr. Rel.* 25:123 (1993).
Ruffin et al., "The Preferential Deposition of Inhaled Isoproterenol and Propanolol in Asthmataic Patients," *Chest* 80:904–907 (1986).
Sela et al., "Multichain Polyamino Acids," *J. Am. Chem. Soc.*78:746 (1956).
Swift, "The oral airway — a conduit or collector for pharmaceutical aerosols?" Respiratory Drug Delivery IV, 187–194 (1994).
Tabata et al., "Controlled Delivery Systems for Proteins Using Polyanhydride Microspheres," *Pharm. Res.*, 10(4): 487–496 (1993).
Tabata and Ikada, "Effect of surface wettability of microspheres on phagocytosis," *J. Colloid and Interface Sci.*, 127(1): 132–140 (1989).
Tabata and Ikada, "Macrophage Phagocytosis of Biodegradable Microspheres Composed of L–lactic Acid/Glycolic Acid Homo– and Copolymers," *J. Biomed. Mater. Res.*, 22: 837–858 (1988).
Tabata and Ikada, "Effect of size and surface charge of polymer microspheres on their phagocytosis by macrophage," *J. Biomed. Mater. Res.*, 22:837 (1988).
Tansey, "The challenges in the development of metered dose inhalation aerosols using ozone–friendly propellants," *Spray Technol. Market*, 4:26–29 (1994).
Timsina et al., "Drug delivery to the respiratory tract using dry powder inhalers," *Int. J. Pharm.*, 101: 1–13 (1994).
Turner, J. and S. Hering, "Greased and oiled substrates as bounce–free impaction surfaces," *J. Aerosol Sci.*, 18: 215–224 (1987).
**Vincent, *Aerosol Science for Industrial Hygientists*, Pergamon Press, NY (1995).
Visser, "An Invited Review: Van der Waals and Other Cohesive Forces Affecting Powder Fluidization," *Powder Technology* 58: 1–10 (1989).
Wail, "Pulmonary Absorption of Peptides and Proteins," *Drug Delivery*, 2:1–20 (1995).
Warheit and Hartsky, "Role of alveolar macrophage chemotaxis and phagocytosis in pulmonary clearance to inhaled particles: Comparisons among rodent species," *Microscopy Res. Tech.*, 26: 412–422 (1993).
**Weibel, Morphometry of the Human Lung, New York: Academic Press (1963).
Wong and Suslick, "Sonochemically produced hemoglobin microbubbles," *Mat. Res. Soc. Symp. Proc.*, 372:89–95 (1995).
Zanen et al., "The optimal particle size for β–adrenergic aerosols in mild asthmatics," *Int. J. Pharm.*, 107: 211–217 (1994).
Zanen et al., "The optimal particle size for parasympathicolytic aerosols in mild asthmatics" *Int. J. Pharm.*, 114:111–115 (1995).
Zeng et al., "The controlled delivery of drugs to the lung," *Int. J. Pharm.*, 124:149–164 (1995).

AERODYNAMICALLY LIGHT PARTICLES FOR PULMONARY DRUG DELIVERY

This application is a continuation in part of U.S. Ser. No. 08/655,570 filed May 24, 1996, the disclosure of which is incorporated herein.

BACKGROUND OF THE INVENTION

The present invention relates generally to biodegradable particles of low density and large size for drug delivery to the pulmonary system.

Biodegradable particles have been developed for the controlled-release and delivery of protein and peptide drugs. Langer, R., *Science*, 249:1527–1533 (1990). Examples include the use of biodegradable particles for gene therapy (Mulligan, R. C. *Science*, 260:926–932 (1993)) and for 'single-shot' immunization by vaccine delivery (Eldridge et al., *Mol. Immunol.*, 28:287–294 (1991)).

Aerosols for the delivery of therapeutic agents to the respiratory tract have been developed. Adjei, A. and Garren, *J. Pharm. Res.* 7, 565–569 (1990); and Zanen, P. and Lamm, J.-W. J. *Int. J. Pharm.* 114, 111–115 (1995). The respiratory tract encompasses the upper airways, including the oropharynx and larynx, followed by the lower airways, which include the trachea followed by bifurcations into the bronchi and bronchioli. The upper and lower airways are called the conducting airways. The terminal bronchioli then divide into respiratory bronchioli which then lead to the ultimate respiratory zone, the alveoli, or deep lung. Gonda, I. "Aerosols for delivery of therapeutic and diagnostic agents to the respiratory tract," in *Critical Reviews in Therapeutic Drug Carrier Systems* 6:273–313, 1990. The deep lung, or alveoli, are the primary target of inhaled therapeutic aerosols for systemic drug delivery.

Inhaled aerosols have been used for the treatment of local lung disorders including asthma and cystic fibrosis (Anderson et al., *Am. Rev. Respir. Dis.*, 140:1317–1324 (1989)) and have potential for the systemic delivery of peptides and proteins as well (Patton and Platz, *Advanced Drug Delivery Reviews*, 8:179–196 (1992)). However, pulmonary drug delivery strategies present many difficulties for the delivery of macromolecules; these include protein denaturation during aerosolization, excessive loss of inhaled drug in the oropharyngeal cavity (often exceeding 80%), poor control over the site of deposition, irreproducibility of therapeutic results owing to variations in breathing patterns, the often too-rapid absorption of drug potentially resulting in local toxic effects, and phagocytosis by lung macrophages.

Considerable attention has been devoted to the design of therapeutic aerosol inhalers to improve the efficiency of inhalation therapies. Timsina et. al., *Int. J. Pharm.* 101, 1–13 (1995); and Tansey, I. P., *Spray Technol. Market* 4, 26–29 (1994). Attention has also been given to the design of dry powder aerosol surface texture, regarding particularly the need to avoid particle aggregation, a phenomenon which considerably diminishes the efficiency of inhalation therapies owing to particle aggregation. French, D. L., Edwards, D. A. and Niven, R. W., *J. Aerosol Sci.* 27, 769–783 (1996). Attention has not been given to the possibility of using large particle size (>5 $\mu$m) as a means to improve aerosolization efficiency, despite the fact that intraparticle adhesion diminishes with increasing particle size. French, D. L., Edwards, D. A. and Niven, R. W. *J. Aerosol Sci.* 27, 769–783 (1996). This is because particles of standard mass density (mass density near 1 g/cm$^3$) and mean diameters >5 $\mu$m are known to deposit excessively in the upper airways or the inhaler device. Heyder, J. et al., *J. Aerosol Sci.*, 17: 811–825 (1986). For this reason, dry powder aerosols for inhalation therapy are generally produced with mean diameters primarily in the range of <5 $\mu$m. Ganderton, D., *J. Biopharnaceutical Sciences* 3:101–105 (1992); and Gonda, I. "Physico-Chemical Principles in Aerosol Delivery," in *Topics in Pharmaceutical Sciences* 1991, Crommelin, D. J. and K. K. Midha, Eds., Medpharm Scientific Publishers, Stuttgart, pp. 95–115, 1992. Large "carrier" particles (containing no drug) have been co-delivered with therapeutic aerosols to aid in achieving efficient aerosolization among other possible benefits. French, D. L., Edwards, D. A. and Niven, R. W. *J. Aerosol Sci.* 27, 769–783 (1996).

Local and systemic inhalation therapies can often benefit from a relatively slow controlled release of the therapeutic agent. Gonda, I., "Physico-chemical principles in aerosol delivery," in: *Topics in Pharmaceutical Sciences* 1991, D. J. A. Crommelin and K. K. Midha, Eds., Stuttgart: Medpharm Scientific Publishers, pp. 95–117, (1992). Slow release from a therapeutic aerosol can prolong the residence of an administered drug in the airways or acini, and diminish the rate of drug appearance in the bloodstream. Also, patient compliance is increased by reducing the frequency of dosing. Langer, R., *Science*, 249:1527–1533 (1990); and Gonda, I. "Aerosols for delivery of therapeutic and diagnostic agents to the respiratory tract," in *Critical Reviews in Therapeutic Drug Carrier Systems* 6:273–313, (1990).

The human lungs can remove or rapidly degrade hydrolytically cleavable deposited aerosols over periods ranging from minutes to hours. In the upper airways, ciliated epithelia contribute to the "mucociliary escalator" by which particles are swept from the airways toward the mouth. Pavia, D. "Lung Mucociliary Clearance," in *Aerosols and the Lung: Clinical and Experimental Aspects*, Clarke, S. W. and Pavia, D., Eds., Butterworths, London, 1984. Anderson et al., *Am. Rev. Respir. Dis.*, 140:1317–1324 (1989). In the deep lungs, alveolar macrophages are capable of phagocytosing particles soon after their deposition. Warheit, M. B. and Hartsky, M. A., *Microscopy Res. Tech.* 26:412–422 (1993); Brain, J. D., "Physiology and Pathophysiology of Pulmonary Macrophages," in *The Reticuloendothelial System*, S. M. Reichard and J. Filkins, Eds., Plenum, New York, pp. 315–327, 1985; Dorries, A. M. and Valberg, P. A., *Am. Rev. Resp. Disease* 146, 831–837 (1991); and Gehr, P. et al. *Microscopy Res. and Tech.*, 26, 423–436 (1993). As the diameter of particles exceeds 3 $\mu$m, there is increasingly less phagocytosis by macrophages. Kawaguchi, H. et al., *Biomaterials* 7:61–66 (1986); Krenis, L. J. and Strauss, B., *Proc. Soc. Exp. Med.*, 107:748–750 (1961); and Rudt, S. and Muller, R. H., *J. Contr. Rel.*, 22:263–272 (1992). However, increasing the particle size also minimizes the probability of particles (possessing standard mass density) entering the airways and acini due to excessive deposition in the oropharyngeal or nasal regions. Heyder, J. et al., *J. Aerosol Sci.*, 17: 811–825 (1986). An effective dry-powder inhalation therapy for both short and long term release of therapeutics, either for local or systemic delivery, requires a powder that displays minimum aggregation, as well as a means of avoiding or suspending the lung's natural clearance mechanisms until drugs have been effectively delivered.

There is a need for improved inhaled aerosols for pulmonary delivery of therapeutic agents. There is a need for the development of drug carriers which are capable of delivering the drug in an effective amount into the airways or the alveolar zone of the lung. There further is a need for the development of drug carriers for use as inhaled aerosols which are biodegradable and are capable of controlled release of drug within the airways or in the alveolar zone of the lung.

It is therefore an object of the present invention to provide improved carriers for the pulmonary delivery of therapeutic agents. It is a further object of the invention to provide inhaled aerosols which are effective carriers for delivery of therapeutic agents to the deep lung. It is another object of the invention to provide carriers for pulmonary delivery which avoid phagocytosis in the deep lung. It is a further object of the invention to provide carriers for pulmonary drug delivery which are capable of biodegrading and releasing the drug at a controlled rate.

SUMMARY OF THE INVENTION

Improved aerodynamically light particles for drug delivery to the pulmonary system, and methods for their synthesis and administration are provided. In a preferred embodiment, the particles are made of a biodegradable material, have a tap density less than 0.4 $g/cm^3$ and a mean diameter between 5 $\mu$m and 30 $\mu$m. In one embodiment, for example, at least 90% of the particles have a mean diameter between 5 $\mu$m and 30 $\mu$m. The particles may be formed of biodegradable materials such as biodegradable polymers, proteins, or other water-soluble materials. For example, the particles may be formed of a functionalized polyester graft copolymer consisting of a linear α-hydroxy-acid polyester backbone having at least one amino acid residue incorporated per molecule therein and at least one poly(amino acid) side chain extending from an amino acid group in the polyester backbone. Other examples include particles formed of water-soluble excipients, such as trehalose or lactose, or proteins, such as lysozyme or insulin. The aerodynamically light particles can be used for enhanced delivery of a therapeutic agent to the airways or the alveolar region of the lung. The particles incorporating a therapeutic agent may be effectively aerosolized for administration to the respiratory tract to permit systemic or local delivery of a wide variety of therapeutic agents. They optionally may be co-delivered with larger carrier particles, not carrying a therapeutic agent, which have for example a mean diameter ranging between about 50 $\mu$m and 100 $\mu$m.

BRIEF DESCRIPTION OF THE INVENTION

Figure 1:
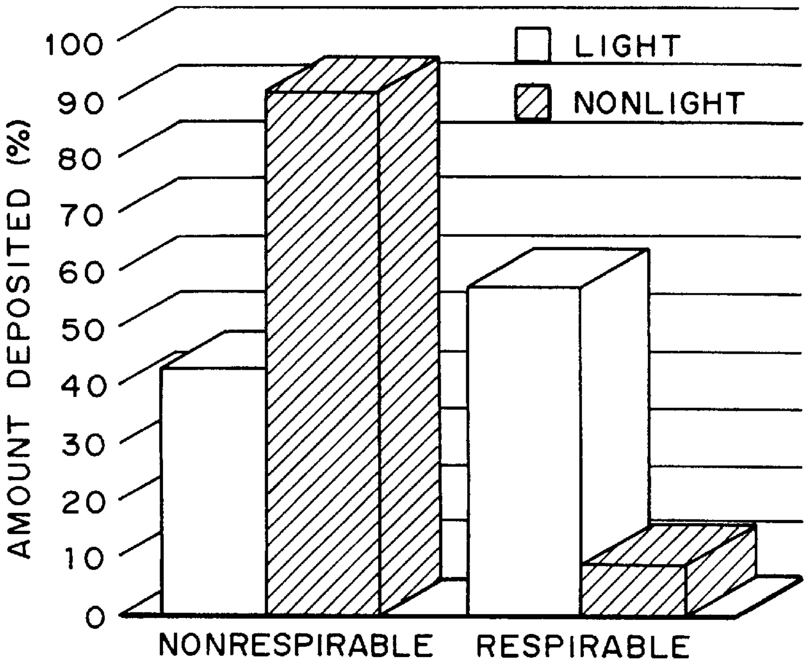
FIG. 1 is a graph comparing total particle mass of aerodynamically light and non-light, control particles deposited on the nonrespirable and respirable stages of a cascade impactor following aerosolization.

Aerodynamically light, biodegradable particles for improved delivery of therapeutic agents to the respiratory tract are provided. The particles can be used in one embodiment for controlled systemic or local drug delivery to the respiratory tract via aerosolization. In a preferred embodiment, the particles have a tap density less than about 0.4 $g/cm^3$. Features of the particle which can contribute to low tap density include irregular surface texture and porous structure. Administration of the low density particles to the lung by aerosolization permits deep lung delivery of relatively large diameter therapeutic aerosols, for example, greater than 5 $\mu$m in mean diameter. A rough surface texture also can reduce particle agglomeration and provide a highly flowable powder, which is ideal for aerosolization via dry powder inhaler devices, leading to lower deposition in the mouth, throat and inhaler device.

Density and Size of Aerodynamically Light Particles

Particle Size

The mass mean diameter of the particles can be measured using a Coulter Counter. The aerodynamically light particles are preferably at least about 5 microns in diameter. The diameter of particles in a sample will range depending upon depending on factors such as particle composition and methods of synthesis. The distribution of size of particles in a sample can be selected to permit optimal deposition within targeted sites within the respiratory tract.

The aerodynamically light particles may be fabricated or separated, for example by filtration, to provide a particle sample with a preselected size distribution. For example, greater than 30%, 50%, 70%, or 80% of the particles in a sample can have a diameter within a selected range of at least 5 $\mu$m. The selected range within which a certain percentage of the particles must fall may be for example, between about 5 and 30 $\mu$m, or optionally between 5 and 15 $\mu$m. In one preferred embodiment, at least a portion of the particles have a diameter between about 9 and 11 $\mu$m. Optionally, the particle sample also can be fabricated wherein at least 90%, or optionally 95% or 99%, have a diameter within the selected range. The presence of the higher proportion of the aerodynamically light, larger diameter (at least about 5 $\mu$m) particles in the particle sample enhances the delivery of therapeutic or diagnostic agents incorporated therein to the deep lung.

In one embodiment, in the particle sample, the interquartile range may be 2 $\mu$m, with a mean diameter for example of 7.5, 8.0, 8.5, 9.0, 9.5, 10.0, 10.5, 11.0, 11.5, 12.0, 12.5, 13.0 or 13.5 $\mu$m. Thus, for example, at least 30%, 40%, 50% or 60% of the particles may have diameters within the selected range 5.5–7.5 $\mu$m, 6.0–8.0 $\mu$m, 6.5–8.5 $\mu$m, 7.0–9.0 $\mu$m, 7.5–9.5 $\mu$m, 8.0–10.0 $\mu$m, 8.5–10.5 $\mu$m, 9.0–11.0 $\mu$m, 9.5–11.5 $\mu$m, 10.0–12.0 $\mu$m, 10.5–12.5$\mu$m, 11.0–13.0 $\mu$m, 11.5–13.5 $\mu$m, 12.0–14.0 $\mu$m, 12.5–14.5 $\mu$m or 13.0–15.0 $\mu$m. Preferably the percentages of particles have diameters within a 1 $\mu$m range, for example, 6.0–7.0 $\mu$m, 10.0–11.0 $\mu$m or 13.0–14.0 $\mu$m.

The aerodynamically light particles incorporating a therapeutic drug, and having a tap density less than about 0.4 $g/cm^3$, with mean diameters of at least about 5 $\mu$m, are more capable of escaping inertial and gravitational deposition in the oropharyngeal region, and are targeted to the airways or the deep lung. The use of larger particles (mean diameter at least about 5 $\mu$m) is advantageous since they are able to aerosolize more efficiently than smaller, non-light aerosol particles such as those currently used for inhalation therapies.

In comparison to smaller non-light particles, the larger (at least about 5 $\mu$m) aerodynamically light particles also can potentially more successfully avoid phagocytic engulfment by alveolar macrophages and clearance from the lungs, due to size exclusion of the particles from the phagocytes' cytosolic space. Phagocytosis of particles by alveolar macrophages diminishes precipitously as particle diameter increases beyond 3 $\mu$m. Kawaguchi, H. et al., *Biomaterials* 7:61–66 (1986); Krenis, L. J. and Strauss, B., *Proc. Soc. Exp. Med.*, 107:748–750 (1961); and Rudt, S. and Muller, R.

H., *J. Contr. Rel.*, 22:263–272 (1992). For particles of statistically isotropic shape (on average, particles of the powder possess no distinguishable orientation), such as spheres with rough surfaces, the particle envelope volume is approximately equivalent to the volume of cytosolic space required within a macrophage for complete particle phagocytosis.

Aerodynamically light particles thus are capable of a longer term release of a therapeutic agent. Following inhalation, aerodynamically light biodegradable particles can deposit in the lungs (due to their relatively low tap density), and subsequently undergo slow degradation and drug release, without the majority of the particles being phagocytosed by alveolar macrophages. The drug can be delivered relatively slowly into the alveolar fluid, and at a controlled rate into the blood stream, minimizing possible toxic responses of exposed cells to an excessively high concentration of the drug. The aerodynamically light particles thus are highly suitable for inhalation therapies, particularly in controlled release applications. The preferred mean diameter for aerodynamically light particles for inhalation therapy is at least about 5 $\mu$m, for example between about 5 and 30 $\mu$m.

The particles may be fabricated with the appropriate material, surface roughness, diameter and tap density for localized delivery to selected regions of the respiratory tract such as the deep lung or upper airways. For example, higher density or larger particles may be used for upper airway delivery, or a mixture of different sized particles in a sample, provided with the same or different therapeutic agent may be administered to target different regions of the lung in one administration.

Particle Density and Deposition

The particles having a diameter of at least about 5 $\mu$m and incorporating a therapeutic or diagnostic agent preferably are aerodynamically light. As used herein, the phrase "aerodynamically light particles" refers to particles having a tap density less than about 0.4 g/cm$^3$. The tap density of particles of a dry powder may be obtained using a GeoPyc™ (Micrometrics Instrument Corp., Norcross, Ga. 30093). Tap density is a standard measure of the envelope mass density. The envelope mass density of an isotropic particle is defined as the mass of the particle divided by the minimum sphere envelope volume within which it can be enclosed.

Inertial impaction and gravitational settling of aerosols are predominant deposition mechanisms in the airways and acini of the lungs during normal breathing conditions. Edwards, D. A., *J. Aerosol Sci.* 26:293–317 (1995). The importance of both deposition mechanisms increases in proportion to the mass of aerosols and not to particle (or envelope) volume. Since the site of aerosol deposition in the lungs is determined by the mass of the aerosol (at least for particles of mean aerodynamic diameter greater than approximately 1 $\mu$m), diminishing the tap density by increasing particle surface irregularities and particle porosity permits the delivery of larger particle envelope volumes into the lungs, all other physical parameters being equal.

The low tap density particles have a small aerodynamic diameter in comparison to the actual envelope sphere diameter. The aerodynamic diameter, $d_{aer}$, is related to the envelope sphere diameter, d (Gonda, I., "Physico-chemical principles in aerosol delivery," in *Topics in Pharmaceutical Sciences* 1991 (eds. D. J. A. Crommelin and K. K. Midha), pp. 95–117, Stuttgart: Medpharm Scientific Publishers, 1992) by the formula:

$$d_{aer}=d\sqrt{\rho}$$

where the envelope mass ρ is in units of g/cm$^3$. Maximal deposition of monodisperse aerosol particles in the alveolar region of the human lung (~60%) occurs for an aerodynamic diameter of approximately $d_{aer}$=3 $\mu$m. Heyder, J. et al., *J. Aerosol Sci.*, 17:811–825 (1986). Due to their small envelope mass density, the actual diameter d of aerodynamically light particles comprising a monodisperse inhaled powder that will exhibit maximum deep-lung deposition is:

$$d=3/\sqrt{\rho}\ \mu m (\text{where } \rho<1 \text{ g/cm}^3);$$

where d is always greater than 3 $\mu$m. For example, aerodynamically light particles that display an envelope mass density, ρ=0.1 g/cm$^3$, will exhibit a maximum deposition for particles having envelope diameters as large as 9.5 $\mu$m. The increased particle size diminishes interparticle adhesion forces. Visser, J., *Powder Technology*, 58:1–10. Thus, large particle size increases efficiency of aerosolization to the deep lung for particles of low envelope mass density, in addition to contributing to lower phagocytic losses.

Particle Materials

In order to serve as efficient and safe drug carriers in drug delivery systems, the aerodynamically light particles preferably are biodegradable and biocompatible, and optionally are capable of biodegrading at a controlled rate for delivery of a drug. The particles can be made of any material which is capable of forming a particle having a tap density less than about 0.4 g/cm$^3$. Both inorganic and organic materials can be used. For example, ceramics may be used. Other non-polymeric materials (e.g. fatty acids) may be used which are capable of forming aerodynamically light particles as defined herein. Different properties of the particle can contribute to the aerodynamic lightness including the composition forming the particle, and the presence of irregular surface structure or pores or cavities within the particle.

Polymeric Particles

The particles may be formed from any biocompatible, and preferably biodegradable polymer, copolymer, or blend, which is capable of forming particles having a tap density less than about 0.4 g/cm$^3$.

Surface eroding polymers such as polyanhydrides may be used to form the aerodynamically light particles. For example, polyanhydrides such as poly[(ρ-carboxyphenoxy)-hexane anhydride] (PCPH) may be used. Biodegradable polyanhydrides are described, for example, in U.S. Pat. No. 4,857,311, the disclosure of which is incorporated herein by reference.

In another embodiment, bulk eroding polymers such as those based on polyesters including poly(hydroxy acids) can be used. For example, polyglycolic acid (PGA) or polylactic acid (PLA) or copolymers thereof may be used to form the aerodynamically light particles, wherein the polyester has incorporated therein a charged or functionalizable group such as an amino acid as described below.

Other polymers include polyamides, polycarbonates, polyalkylenes such as polyethylene, polypropylene, poly(ethylene glycol), poly(ethylene oxide), poly(ethylene terephthalate), poly vinyl compounds such as polyvinyl alcohols, polyvinyl ethers, and polyvinyl esters, polymers of acrylic and methacrylic acids, celluloses and other polysaccharides, and peptides or proteins, or copolymers or blends thereof which are capable of forming aerodynamically light particles with a tap density less than about 0.4 g/cm$^3$. Polymers may be selected with or modified to have the appropriate stability and degradation rates in vivo for different controlled drug delivery applications.

Polyester Graft Copolymers

In one preferred embodiment, the aerodynamically light particles are formed from functionalized polyester graft copolymers, as described in Hrkach et al., *Macromolecules*, 28:4736–4739 (1995); and Hrkach et al., "Poly(L-Lactic acid-co-amino acid) Graft Copolymers: A Class of Functional Biodegradable Biomaterials" in *Hydrogels and Biodegradable Polymers for Bioapplications*, ACS Symposium Series No. 627, Raphael M. Ottenbrite et al., Eds., American Chemical Society, Chapter 8, pp. 93–101, 1996, the disclosures of which are incorporated herein by reference. The functionalized graft copolymers are copolymers of polyesters, such as poly(glycolic acid) or poly(lactic acid), and another polymer including functionalizable or ionizable groups, such as a poly(amino acid). In a preferred embodiment, comb-like graft copolymers are used which include a linear polyester backbone having amino acids incorporated therein, and poly(amino acid) side chains which extend from the amino acid residues in the polyester backbone. The polyesters may be polymers of α-hydroxy acids such as lactic acid, glycolic acid, rhydroxybutyric acid and hydroxy valeric acid, or derivatives or combinations thereof. The inclusion of ionizable side chains, such as polylysine, in the polymer has been found to enable the formation of more aerodynamically light particles, using techniques for making microparticles known in the art, such as solvent evaporation. Other ionizable groups, such as amino or carboxyl groups, may be incorporated, covalently or noncovalently, into the polymer to enhance surface roughness and porosity. For example, polyalanine could be incorporated into the polymer.

An exemplary polyester graft copolymer, which may be used to form aerodynamically light polymeric particles is the graft copolymer, poly(lactic acid-co-lysine-graft-lysine) (PLAL-Lys), which has a polyester backbone consisting of poly(L-lactic acid-co- L-lysine) (PLAL), and grafted polylysine chains. PLAL-Lys is a comb-like graft copolymer having a backbone composition, for example, of 98 mol % lactic acid and 2 mol % lysine and poly(lysine) side chains extending from the lysine sites of the backbone.

PLAL-Lys may be synthesized as follows. First, the PLAL copolymer consisting of L-lactic acid units and approximately 1–2% N ϵ carbobenzoxy-L-lysine (Z-L-lysine) units is synthesized as described in Barrera et al., *J. Am. Chem. Soc.*, 115:11010 (1993). Removal of the Z protecting groups of the randomly incorporated lysine groups in the polymer chain of PLAL yields the free ϵ-amine which can undergo further chemical modification. The use of the poly(lactic acid) copolymer is advantageous since it biodegrades into lactic acid and lysine, which can be processed by the body. The existing backbone lysine groups are used as initiating sites for the growth of poly(amino acid) side chains.

The lysine ϵ-amino groups of linear poly(L-lactic acid-co-L-lysine) copolymers initiate the ring opening polymerization of an amino acid N-ϵ carboxyanhydride (NCA) to produce poly(L-lactic acid-co-amino acid) comb-like graft copolymers. In a preferred embodiment, NCAs are synthesized by reacting the appropriate amino acid with triphosgene. Daly et al., *Tetrahedron Lett.*, 29:5859 (1988). The advantage of using triphosgene over phosgene gas is that it is a solid material, and therefore, safer and easier to handle. It also is soluble in THF and hexane so any excess is efficiently separated from the NCAs.

The ring opening polymerization of amino acid N-carboxyanhydrides (NCAs) is initiated by nucleophilic initiators such as amines, alcohols, and water. The primary amine initiated ring opening polymerization of NCAs allows good control over the degree of polymerization when the monomer to initiator ratio (M/I) is less than 150. Kricheldorf, H. R. in *Models of Biopolymers by Ring-Opening Polymerization*, Penczek, S., Ed., CRC Press, Boca Raton, 1990, Chapter 1; Kricheldorf, H. R. *α-Aminoacid-N-Carboxy-Anhydrides and Related Heterocycles*, Springer-Verlag, Berlin, 1987; and Imanishi, Y. in *Ring-Opening Polymerization*, Ivin, K. J. and Saegusa, T., Eds., Elsevier, London, 1984, Volume 2, Chapter 8. Methods for using lysine ϵ-amino groups as polymeric initiators for NCA polymerizations are described in the art. Sela, M. et al., *J. Am. Chem. Soc.*, 78: 746 (1956).

In the reaction of an amino acid NCA with PLAL, the nucleophilic primary ϵ-amino of the lysine side chain attacks C-5 of the NCA leading to ring opening and formation of the amino acid amide, along with the evolution of $CO_2$. Propagation takes place via further attack of the amino group of the amino acid amides on subsequent NCA molecules. The degree of polymerization of the poly(amino acid) side chains, the corresponding amino acid content in the graft copolymers and their resulting physical and chemical characteristics can be controlled by changing the M/I ratio for the NCA polymerization—that is, changing the ratio of NCA to lysine ϵ-amino groups of pLAL. Thus, in the synthesis, the length of the poly(amino acid), such as poly(lysine), side chains and the total amino acid content in the polymer may be designed and synthesized for a particular application.

The poly(amino acid) side chains grafted onto or incorporated into the polyester backbone can include any amino acid, such as aspartic acid, alanine or lysine, or mixtures thereof. The functional groups present in the amino acid side chains, which can be chemically modified, include amino, carboxylic acid, thiol, guanido, imidazole and hydroxyl groups. As used herein, the term "amino acid" includes natural and synthetic amino acids and derivatives thereof. The polymers can be prepared with a range of amino acid side chain lengths, for example, about 10–100 or more amino acids, and with an overall amino acid content of, for example, 7–72% or more depending on the reaction conditions. The grafting of poly(amino acids) from the pLAL backbone may be conducted in a solvent such as dioxane, DMF, or $CH_2Cl_2$, or mixtures thereof. In a preferred embodiment, the reaction is conducted at room temperature for about 2–4 days in dioxane.

Alternatively, the aerodynamically light particles for pulmonary drug delivery may be formed from polymers or blends of polymers with different polyester/amino acid backbones and grafted amino acid side chains. For example, poly(lactic acid-co-lysine-graft-alanine-lysine) (PLAL-Ala-Lys), or a blend of PLAL-Lys with poly(lactic acid-co-glycolic acid-block-ethylene oxide) (PLGA-PEG) (PLAL-Lys-PLGA-PEG) may be used.

In the synthesis, the graft copolymers may be tailored to optimize different characteristics of the aerodynamically light particle including: i) interactions between the agent to be delivered and the copolymer to provide stabilization of the agent and retention of activity upon delivery; ii) rate of polymer degradation and, thereby, rate of drug release profiles; iii) surface characteristics and targeting capabilities via chemical modification; and iv) particle porosity.

Formation of Aerodynamically Light Polymeric Particles

Aerodynamically light polymeric particles may be prepared using single and double emulsion solvent evaporation, spray drying, solvent extraction and other methods well known to those of ordinary skill in the art. The aerodynamically light particles may be made, for example using methods for making microspheres or microcapsules known in the art.

Methods developed for making microspheres for drug delivery are described in the literature, for example, as described by Mathiowitz and Langer, *J. Controlled Release* 5,13–22 (1987); Mathiowitz, et al., *Reactive Polymers* 6, 275–283 (1987); and Mathiowitz, et al., *J. Appl. Polymer Sci.* 35, 755–774 (1988), the teachings of which are incorporated herein. The selection of the method depends on the polymer selection, the size, external morphology, and crystallinity that is desired, as described, for example, by Mathiowitz, et al., *Scanning Microscopy* 4,329–340 (1990); Mathiowitz, et al., *J. Appl. Polymer Sci.* 45, 125–134 (1992); and Benita, et al., *J. Pharm. Sci.* 73, 1721–1724 (1984), the teachings of which are incorporated herein.

In solvent evaporation, described for example, in Mathiowitz, et al., (1990), Benita, and U.S. Pat. No. 4,272,398 to Jaffe, the polymer is dissolved in a volatile organic solvent, such as methylene chloride. Several different polymer concentrations can be used, for example, between 0.05 and 0.20 g/ml. The drug, either in soluble form or dispersed as fine particles, is added to the polymer solution, and the mixture is suspended in an aqueous phase that contains a surface active agent such as poly(vinyl alcohol). The aqueous phase may be, for example, a concentration of 1% poly(vinyl alcohol) w/v in distilled water. The resulting emulsion is stirred until most of the organic solvent evaporates, leaving solid microspheres, which may be washed with water and dried overnight in a lyophilizer.

Microspheres with different sizes (1–1000 microns) and morphologies can be obtained by this method which is useful for relatively stable polymers such as polyesters and polystyrene. However, labile polymers such as polyanhydrides may degrade due to exposure to water. For these polymers, solvent removal may be preferred.

Solvent removal was primarily designed for use with polyanhydrides. In this method, the drug is dispersed or dissolved in a solution of a selected polymer in a volatile organic solvent like methylene chloride. The mixture is then suspended in oil, such as silicon oil, by stirring, to form an emulsion. Within 24 hours, the solvent diffuses into the oil phase and the emulsion droplets harden into solid polymer microspheres. Unlike solvent evaporation, this method can be used to make microspheres from polymers with high melting points and a wide range of molecular weights. Microspheres having a diameter for example between one and 300 microns can be obtained with this procedure.

Targeting of Particles

Targeting molecules can be attached to the aerodynamically light particles via reactive functional groups on the particles. For example, targeting molecules can be attached to the amino acid groups of functionalized polyester graft copolymer particles, such as PLAL-Lys particles. Targeting molecules permit binding interaction of the particle with specific receptor sites, such as those within the lungs. The particles can be targeted by attachment of ligands which specifically or non-specifically bind to particular targets. Exemplary targeting molecules include antibodies and fragments thereof including the variable regions, lectins, and hormones or other organic molecules capable of specific binding for example to receptors on the surfaces of the target cells.

Therapeutic Agents

Any of a variety of therapeutic, prophylactic or diagnostic agents can be incorporated within the aerodynamically light particles. The aerodynamically light particles can be used to locally or systemically deliver a variety of therapeutic agents to an animal. Examples include synthetic inorganic and organic compounds, proteins and peptides, polysaccharides and other sugars, lipids, and nucleic acid sequences having therapeutic, prophylactic or diagnostic activities. Nucleic acid sequences include genes, antisense molecules which bind to complementary DNA to inhibit transcription, and ribozymes. The agents to be incorporated can have a variety of biological activities, such as vasoactive agents, neuroactive agents, hormones, anticoagulants, immunomodulating agents, cytotoxic agents, prophylactic agents, antibiotics, antivirals, antisense, antigens, and antibodies. In some instances, the proteins may be antibodies or antigens which otherwise would have to be administered by injection to elicit an appropriate response. Compounds with a wide range of molecular weight can be encapsulated, for example, between 100 and 500,000 grams per mole.

Proteins are defined as consisting of 100 amino acid residues or more; peptides are less than 100 amino acid residues. Unless otherwise stated, the term protein refers to both proteins and peptides. Examples include insulin and other hormones. Polysaccharides, such as heparin, can also be administered.

The aerodynamically light polymeric aerosols are useful as carriers for a variety of inhalation therapies. They can be used to encapsulate small and large drugs, release encapsulated drugs over time periods ranging from hours to months, and withstand extreme conditions during aerosolization or following deposition in the lungs that might otherwise harm the encapsulated therapeutic.

The aerodynamically light particles may include a therapeutic agent for local delivery within the lung, such as agents for the treatment of asthma, emphysema, or cystic fibrosis, or for systemic treatment. For example, genes for the treatment of diseases such as cystic fibrosis can be administered, as can beta agonists for asthma. Other specific therapeutic agents include, but are not limited to, insulin, calcitonin, leuprolide (or LHRH), G-CSF, parathyroid hormone-related peptide, somatostatin, testosterone, progesterone, estradiol, nicotine, fentanyl, norethisterone, clonidine, scopolomine, salicylate, cromolyn sodium, salmeterol, formeterol, albeterol, and vallium.

Administration

The particles including a therapeutic agent may be administered alone or in any appropriate pharmaceutical carrier, such as a liquid, for example saline, or a powder, for administration to the respiratory system. They can be co-delivered with larger carrier particles, not including a therapeutic agent, the latter possessing mass mean diameters for example in the range 50 $\mu$m–100 $\mu$m.

Aerosol dosage, formulations and delivery systems may be selected for a particular therapeutic application, as described, for example, in Gonda, I. "Aerosols for delivery of therapeutic and diagnostic agents to the respiratory tract," in *Critical Reviews in Therapeutic Drug Carrier Systems*, 6:273–313, 1990; and in Moren, "Aerosol dosage forms and formulations," in: *Aerosols in Medicine. Principles, Diagnosis and Therapy*, Moren, et al., Eds, Esevier, Amsterdam, 1985, the disclosures of which are incorporated herein by reference.

The greater efficiency of aerosolization by aerodynamically light particles of relatively large size permits more drug to be delivered than is possible with the same mass of non-light aerosols. The relatively large size of aerodynamically light aerosols depositing in the deep lungs also minimizes potential drug losses caused by particle phagocytosis. The use of aerodynamically light polymeric aerosols as therapeutic carriers provides the benefits of biodegradable polymers for controlled release in the lungs and long-time local action or systemic bioavailability. Denaturation of macromolecular drugs can be minimized during aerosolization since macromolecules are contained and protected within a polymeric shell. Coencapsulation of peptides with peptidase-inhibitors can minimize peptide enzymatic degradation.

The present invention will be further understood by reference to the following non-limiting examples.

EXAMPLE 1

Synthesis of Aerodynamically Light Poly[(p-carboxyphenoxy)-hexane anhydride] ("PCPH") Particles Aerodynamically light poly[(p-carboxyphenoxy)-hexane anhydride] ("PCPH") particles were synthesized as follows. 100 mg PCPH (MW~25,000) was dissolved in 3.0 mL methylene chloride. To this clear solution was added 5.0 mL 1% w/v aqueous polyvinyl alcohol (PVA, MW~25,000, 88 mole % hydrolyzed) saturated with methylene chloride, and the mixture was vortexed (Vortex Genie 2, Fisher Scientific) at maximum speed for one minute. The resulting milky-white emulsion was poured into a beaker containing 95 mL 1% PVA and homogenized (Silverson Homogenizers) at 6000 RPM for one minute using a 0.75 inch tip. After homogenization, the mixture was stirred with a magnetic stirring bar and the methylene chloride quickly extracted from the polymer particles by adding 2 mL isopropyl alcohol. The mixture was continued to stir for 35 minutes to allow complete hardening of the microparticles. The hardened particles were collected by centrifugation and washed several times with double distilled water. The particles were freeze dried to obtain a free-flowing powder void of clumps. Yield, 85–90%.

The mean diameter of this batch was 6.0 μm, however, particles with mean diameters ranging from a few hundred nanometers to several millimeters may be made with only slight modifications. Scanning electron micrograph photos of a typical batch of PCPH particles showed the particles to be highly porous with irregular surface shape. The particles have a tap density less than 0.4 g/cm$^3$.

EXAMPLE 2

Synthesis of PLAL-Lys and PLAL-Lys-Ala Polymeric and Copolymeric Particles

Aerodynamically Light PLAL-Lys Particles

PLAL-Lys particles were prepared by dissolving 50 mg of the graft copolymer in 0.5 ml dimethylsulfoxide, then adding 1.5 ml dichloromethane dropwise. The polymer solution is emulsified in 100 ml of 5% w/v polyvinyl alcohol solution (average molecular weight 25 KDa, 88% hydrolyzed) using a homogenizer (Silverson) at a speed of approximately 7500 rpm. The resulting dispersion is stirred using a magnetic stirrer for 1 hour. Following this period, the pH is brought to 7.0–7.2 by addition of 0.1N NaOH solution. Stirring is continued for an additional 2 hours until the methylene chloride is completely evaporated and the particles hardened. The particles are then isolated by centrifugation at 4000 rpm (1600 g) for 10 minutes (Sorvall RC-5B). The supernatant is discarded and the precipitate washed three times with distilled water followed by centrifugation for 10 minutes at 4000 rpm each time. Finally, the particles are resuspended in 5 ml of distilled water, the dispersion frozen in liquid nitrogen, and lyophilized (Labconco freeze dryer 8) for at least 48 hours. Particle sizing is performed using a Coulter counter. Average particle mean diameters ranged from 100 nm to 14 μm, depending upon processing parameters such as homogenization speed and time. All particles exhibited tap densities less than 0.4 g/cm$^3$. Scanning electron micrograph photos of the particles showed them to be highly porous with irregular surfaces.

Aerodynamically Light PLAL-Ala-Lys Particles 100 mg of PLAL-Ala-Lys is completely dissolved in 0.4 ml trifluoroethanol, then 1.0 ml methylene chloride is added dropwise. The polymer solution is emulsified in 100 ml of 1% w/v polyvinyl alcohol solution (average molecular weight 25 KDa, 80% hydrolyzed) using a sonicator (Sonic&Materal VC-250) for 15 seconds at an output of 40 W. 2 ml of 1% PVA solution is added to the mixture and it is vortexed at the highest speed for 30 seconds. The mixture is quickly poured into a beaker containing 100 ml 0.3% PVA solution, and stirred for three hours allowing evaporation of the methylene chloride. Scanning electron micrograph photos of the particles showed them to possess highly irregular surfaces.

Aerodynamically Light Copolymer Particles

Polymeric aerodynamically light particles consisting of a blend of PLAL-Lys and PLGA-PEG were made. 50 mg of the PLGA-PEG polymer (molecular weight of PEG: 20 KDa, 1:2 weight ratio of PEG:PLGA, 75:25 lactide:glycolide) was completely dissolved in 1 ml dichloromethane. 3 mg of poly(lactide-co-lysine)-polylysine graft copolymer is dissolved in 0.1 ml dimethylsulfoxide and mixed with the first polymer solution. 0.2 ml of TE buffer, pH 7.6, is emulsified in the polymer solution by probe sonication (Sonic&Materal VC-250) for 10 seconds at an output of 40 W. To this first emulsion, 2 ml of distilled water is added and mixed using a vortex mixer at 4000 rpm for 60 seconds. The resulting dispersion is agitated by using a magnetic stirrer for 3 hours until methylene chloride is completely evaporated and microspheres formed. The spheres are then isolated by centrifugation at 5000 rpm for 30 min. The supernatant is discarded, the precipitate washed three times with distilled water and resuspended in 5 ml of water. The dispersion is frozen in liquid nitrogen and lyophilized for 48 hours.

Variables which may be manipulated to alter the size distribution of the particles include: polymer concentration, polymer molecular weight, surfactant type (e.g., PVA, PEG, etc.), surfactant concentration, and mixing intensity. Variables which may be manipulated to alter the surface shape and porosity of the particles include: polymer concentration, polymer molecular weight, rate of methylene chloride extraction by isopropyl alcohol (or another miscible solvent), volume of isopropyl alcohol added, inclusion of an inner water phase, volume of inner water phase, inclusion of salts or other highly water-soluble molecules in the inner water phase which leak out of the hardening sphere by osmotic pressure, causing the formation of channels, or pores, in proportion to their concentration, and surfactant type and concentration.

By scanning electron microscopy (SEM), the PLAL-Lys-PLGA-PEG particles were highly surface rough and porous. The particles had a mean particle diameter of 7 μm. The blend of PLAL-Lys with poly(lactic acid) (PLA) and/or PLGA-PEG copolymers can be adjusted to adjust particle porosity and size. Additionally, processing parameters such as homogenization speed and time can be adjusted. Neither PLAL, PLA nor PLGA-PEG alone yields an aerodynamically light structure when prepared by these techniques.

EXAMPLE 3

Synthesis of Spray-Dried Particles

Aerodynamically Light Particles Containing Polymer and Drug Soluble in Common Solvent Aerodynamically light 50:50 PLGA particles were prepared by spray drying with testosterone encapsulated within the particles according to the following procedures. 2.0 g poly (D,L-lactic-co-glycolic acid) with a molar ratio of 50:50 (PLGA 50:50, Resomer RG503, B.I. Chemicals, Montvale, N.J.) and 0.50 g testosterone (Sigma Chemical Co., St. Louis, Mo.) are completely dissolved in 100 mL dichloromethane at room temperature. The mixture is subsequently spray-dried through a 0.5 mm nozzle at a flow rate of 5 mL/min using a Buchi laboratory spray-drier (model 190, Buchi, Germany). The flow rate of compressed air is 700 nl. The inlet temperature is set to 30° C. and the outlet temperature to 25° C. The aspirator is set to achieve a vacuum of −20 to −25 bar. The yield is 51% and the mean particle size is approximately 5 μm. Larger particle size can be achieved by lowering the inlet compressed air flow rate, as well as by changing other variables. The particles are aerodynamically light, as determined by a tap density less than or equal to 0.4 g/cm$^3$. Porosity and surface roughness can be increased by varying the inlet and outlet temperatures, among other factors.

Aerodynamically Light Particles Containing Polymer and Drug in Different Solvents Aerodynamically light PLA particles with a model hydrophilic drug (dextran) were prepared by spray drying using the following procedure. 2.0 mL of an aqueous 10% w/v FITC-dextran (MW 70,000, Sigma Chemical Co.) solution was emulsified into 100 mL of a 2% w/v solution of poly (D,L-lactic acid) (PLA, Resomer R206, B.I. Chemicals) in dichloromethane by probe sonication (Vibracell Sonicator, Branson). The emulsion is subsequently spray-dried at a flow rate of 5 mL/min with an air flow rate of 700 nl/h (inlet temperature=30° C., outlet temperature=21 ° C., −20 mbar vacuum). The yield is 56%. The particles are aerodynamically light, as determined by a tap density less 0.4 g/cm$^3$.

Aerodynamically Light Protein Particles

Aerodynamically light lysozyme particles were prepared by spray drying using the following procedure. 4.75 g lysozyme (Sigma) was dissolved in 95 mL double distilled water (5% w/v solution) and spray-dried using a 0.5 mm nozzle and a Buchi laboratory spray-drier. The flow rate of compressed air was 725 nl/h. The flow rate of the lysozyme solution was set such that, at a set inlet temperature of 97°–100° C., the outlet temperature is 55°–57° C. The aspirator was set to achieve a vacuum of −30 mbar. The enzymatic activity of lysozyme was found to be unaffected by this process and the yield of the aerodynamically light particles (tap density less than 0.4 g/cm$^3$) was 66%.

Aerodynamically Light High-Molecular Weight Water-Soluble Particles

Aerodynamically light dextran particles were prepared by spray drying using the following procedure. 6.04 g DEAE dextran (Sigma) was dissolved in 242 mL double distilled water (2.5% w/v solution) and spray-dried using a 0.5 mm nozzle and a Buchi laboratory spray-drier. The flow rate of compressed air was 750 nl/h. The flow rate of the DEAE-dextran solution was set such that, at a set inlet temperature of 155° C., the outlet temperature was 80° C. The aspirator was set to achieve a vacuum of −20 mbar. The yield of the aerodynamically light particles (tap density less than 0.4 g/cm$^3$) was 66% and the size range ranged between 1–15 μm.

Aerodynamically Light Low-Molecular Weight Water-Soluble Particles

Aerodynamically light trehalose particles were prepared by spray drying using the following procedure. 4.9 g trehalose (Sigma) was dissolved in 192 mL double distilled water (2.5% w/v solution) and spray-dried using a 0.5 mm nozzle and a Buchi laboratory spray-drier. The flow rate of compressed air 650 nl/h. The flow rate of the trehalose solution was set such that, at a set inlet temperature of 100° C., the outlet temperature was 60° C. The aspirator was set to achieve a vacuum of −30 mbar. The yield of the aerodynamically light particles (tap density less than 0.4 g/cm$^3$) was 36% and the size range ranged between 1–15 μm.

Aerodynamically Light Low-Molecular Weight Water-Soluble Particles

Polyethylene glycol (PEG) is a water-soluble macromolecule, however, it cannot be spray dried from an aqueous solution since it melts at room temperatures below that needed to evaporate water. As a result, we have spray-dried PEG at low temperatures from a solution in dichloromethane, a low boiling organic solvent. Aerodynamically light PEG particles were prepared by spray drying using the following procedure. 5.0 g PEG (MW 15,000–20,000, Sigma) was dissolved in 100 mL double distilled water (5.0% w/v solution) and spray-dried using a 0.5 mm nozzle and a Buchi laboratory spray-drier. The flow rate of compressed air 750 nl/h. The flow rate of the PEG solution was set such that, at a set inlet temperature of 45° C., the outlet temperature was 34°–35° C. The aspirator was set to achieve a vacuum of −22 mbar. The yield of the aerodynamically light particles (tap density less than 0.4 g/cm$^3$) was 67% and the size range ranged between 1–15 μm.

EXAMPLE 4

Rhodamine Isothiocyanate Labeling of PLAL and PLAL-Lys Particles

Aerodynamically light particles were compared with control particles, referred to herein as "non-light" particles. Lysine amine groups on the surface of aerodynamically light (PLAL-Lys) and control, non-light (PLAL) particles, with similar mean diameters (6–7 μm) and size distributions (standard deviations 3–4 μm) were labeled with Rhodamine isothiocyanate. The tap density of the porous PLAL-Lys particles was 0.1 g/cm$^3$ and that of the non-light PLAL particles was 0.8 g/cm$^3$.

The rhodamine-labeled particles were characterized by confocal microscopy. A limited number of lysine functionalities on the surface of the solid particle were able to react with rhodamine isothiocyanate, as evidenced by the fluorescent image. In the aerodynamically light particle, the higher lysine content in the graft copolymer and the porous particle structure result in a higher level of rhodamine attachment, with rhodamine attachment dispersed throughout the intersticies of the porous structure. This also demonstrates that targeting molecules can be attached to the aerodynamically light particles for interaction with specific receptor sites within the lungs via chemical attachment of appropriate targeting agents to the particle surface.

EXAMPLE 5

Aerosolization of PLAL and PLAL-Lys Particles

To determine whether large aerodynamically light particles can escape (mouth, throat and inhaler) deposition and more efficiently enter the airways and acini than nonporous particles of similar size (referred to herein as nonlight or control particles), aerosolization and deposition of aerodynamically light PLAL-Lys (mean diameter 6.3 μm) or control, non-light PLAL (mean diameter 6.9 μm) particles were examined in vitro using a cascade impactor system.

20 mg of the aerodynamically light or non-light microparticles were placed in gelatine capsules (Eli Lilly), the capsules loaded into a Spinhaler dry powder inhaler (DPI) (Fisons), and the DPI activated. Particles were aerosolized into a Mark I Andersen Impactor (Andersen Samplers, GA) from the DPI for 30 seconds at 28.3 l/min flow rate. Each plate of the Andersen Impactor was previously coated with Tween 80 by immersing the plates in an acetone solution (5% w/vol) and subsequently evaporating the acetone in a oven at 60° C. for 5 min. After aerosolization and deposition, particles were collected from each stage of the impactor system in separate volumetric flasks by rinsing each stage with a NaOH solution (0.2N) in order to completely degrade the polymers. After incubation at 37° C. for 12 h, the fluorescence of each solution was measured (wavelengths of 554 nm excitation, 574 nm emission).

Particles were determined as nonrespirable (mean aerodynamic diameter exceeding 4.7 μm: impactor estimate) if they deposited on the first three stages of the impactor, and respirable (mean aerodynamic diameter 4.7 μm or less) if they deposited on subsequent stages. FIG. 1 shows that less than 10% of the non-light (PLAL) particles that exit the DPI are respirable. This is consistent with the large size of the microparticles and their standard mass density. On the other hand, greater than 55% of the aerodynamically light (PLAL-Lys) particles are respirable, even though the geometrical dimensions of the two particle types are almost identical. The lower tap density of the aerodynamically light (PLAL-Lys) microparticles is responsible for this improvement in particle penetration, as discussed further below.

The non-light (PLAL) particles also inefficiently aerosolize from the DPI; typically, less than 40% of the non-light particles exited the Spinhaler DPI for the protocol used. The aerodynamically light (PLAL-Lys) particles exhibited much more efficient aerosolization (approximately 80% of the aerodynamically light microparticles typically exited the DPI during aerosolization).

The combined effects of efficient aerosolization and high respirable fraction of aerosolized particle mass means that a far greater fraction of an aerodynamically light particle powder is likely to deposit in the lungs than of a non-light particle powder.

EXAMPLE 6

In Vivo Aerosolization of PLAL and PLAL-Lys Particles

The penetration of aerodynamically light and non-light polymeric PLAL-Lys and PLAL microparticles into the lungs was evaluated in an in vivo experiment involving the aerosolization of the microparticles into the airways of live rats.

Male Spraque Dawley rats (150–200 g) were anesthetized using ketamine (90 mg/kg)/xylazine (10 mg/kg). The anesthetized rat was placed ventral side up on a surgical table provided with a temperature controlled pad to maintain physiological temperature. The animal was cannulated above the carina with an endotracheal tube connected to a Harvard ventilator. The animal was force ventilated for 20 minutes at 300 ml/min. 50 mg of aerodynamically light (PLAL-Lys) or non-light (PLA) microparticles were introduced into the endotracheal tube.

Following the period of forced ventilation, the animal was euthanized and the lungs and trachea were separately washed using bronchoalveolar lavage. A tracheal cannula was inserted, tied into place, and the airways were washed with 10 ml aliquots of HBSS. The lavage procedure was repeated until a total volume of 30 ml was collected. The lavage fluid was centrifuged (400 g) and the pellets collected and resuspended in 2 ml of phenol red-free Hanks balanced salt solution (Gibco, Grand Island, N.Y.) without $Ca^2$ and $Mg^{2+}$ (HBSS). 100 ml were removed for particle counting using a hemacytometer. The remaining solution was mixed with 10 ml of 0.4N NaOH. After incubation at 37° C. for 12 h, the fluorescence of each solution was measured (wavelengths of 554 nm excitation, 574 nm emission).

Figure 2:
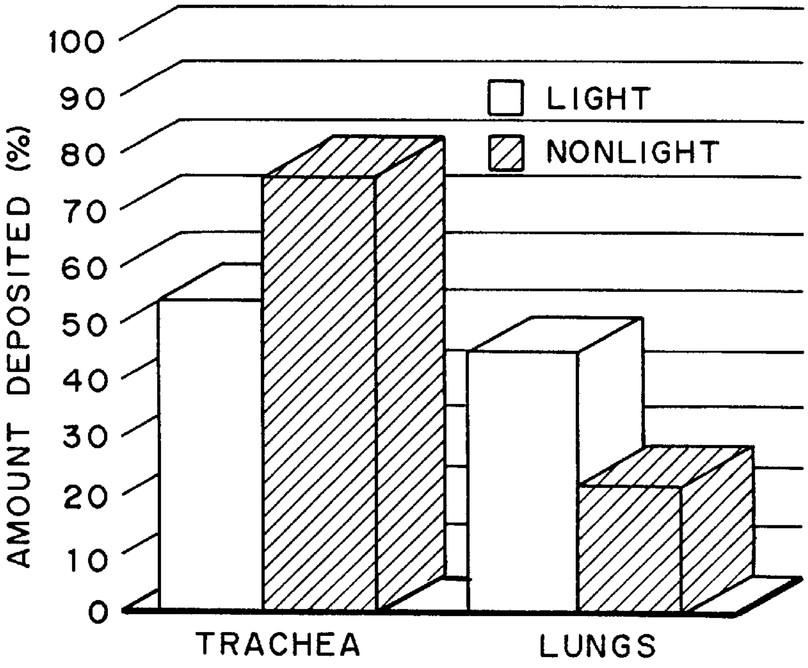
FIG. 2 is a graph comparing total particle mass deposited in the trachea and after the carina (lungs) in rat lungs and upper airways following intratracheal aerosolization during forced ventilation of aerodynamically light PLAL-Lys particles and control, non-light PLA particles.

FIG. 2 is a bar graph showing total particle mass deposited in the trachea and after the carina (lungs) in rat lungs and upper airways following intratracheal aerosolization during forced ventilation. The PLAL-Lys aerodynamically light particles had a mean diameter 6.9 μm. The non-light PLAL particles had a mean diameter of 6.7 μm. Percent tracheal aerodynamically light particle deposition was 54.5, and non-light deposition was 77.0. Percent aerodynamically light particle deposition in the lungs was 46.8 and non-light deposition was 23.0.

The non-light (PLAL) particles deposited primarily in the trachea (approximately 79% of all particle mass that entered the trachea). This result is similar to the in vitro performance of the non-light microparticles and is consistent with the relatively large size of the nonlight particles. Approximately 54% of the aerodynamically light (PLAL-Lys) particle mass deposited in the trachea. Therefore, about half of the aerodynamically light particle mass that enters the trachea traverses through the trachea and into the airways and acini of the rat lungs, demonstrating the effective penetration of the aerodynamically light particles into the lungs.

Figure 3:
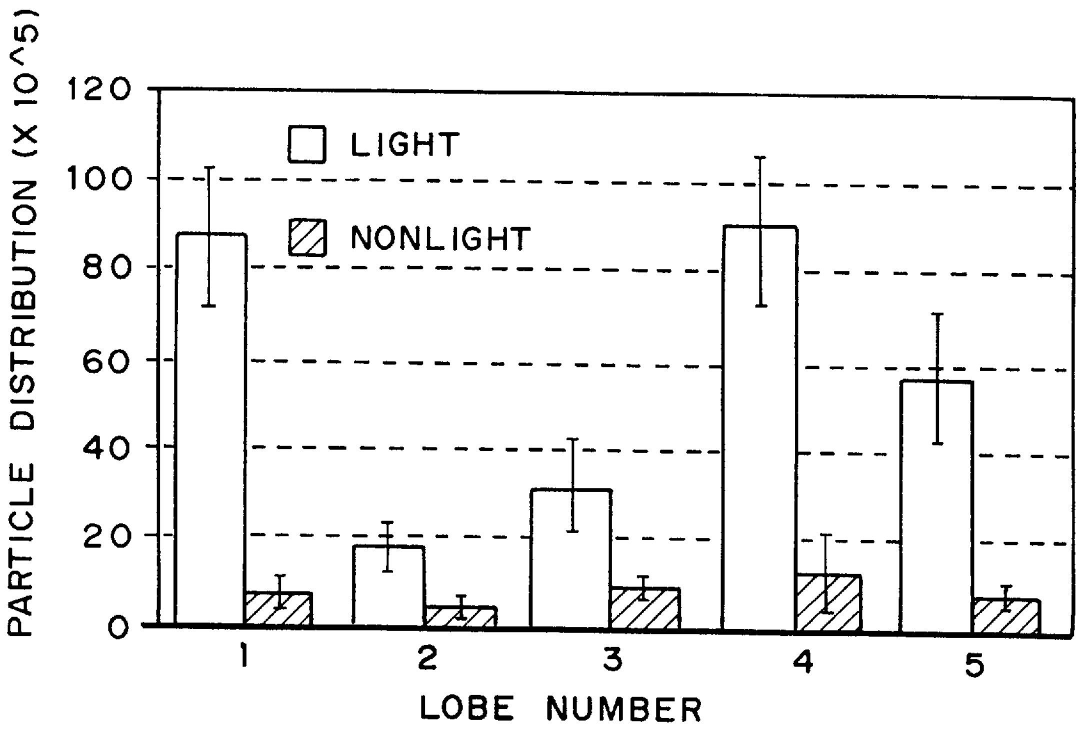
FIG. 3 is a graph comparing total particle recovery of aerodynamically light PLAL-Lys particles and control PLA particles in rat lungs and following bronchoalveolar lavage.

Following bronchoalveolar lavage, particles remaining in the rat lungs were obtained by careful dissection of the individual lobes of the lungs. The lobes were placed in separate petri dishes containing 5 ml of HBSS. Each lobe was teased through 60 mesh screen to dissociate the tissue and was then filtered through cotton gauze to remove tissue debris and connective tissue. The petri dish and gauze were washed with an additional 15 ml of HBSS to maximize microparticle collection. Each tissue preparation was centrifuged and resuspended in 2 ml of HBSS and the number of particles counted in a hemacytometer. The particle numbers remaining in the lungs following the bronchoalveolar lavage are shown in FIG. 3. Lobe numbers correspond to: 1) left lung, 2) anterior, 3) median, 4) posterior, 5) postcaval. A considerably greater number of aerodynamically light PLAL-Lys particles enters every lobe of the lungs than the nonlight PLAL particles, even though the geometrical dimensions of the two types of particles are essentially the same. These results reflect both the efficiency of aerodynamically light particle aerosolization and the propensity of the aerodynamically light particles to escape deposition prior to the carina or first bifurcation.

Modifications and variations of the present invention will be obvious to those skilled in the art from the foregoing detailed description. Such modifications and variations are intended to come within the scope of the following claims.

What is claimed is:

1. A particulate composition for drug delivery to the pulmonary system comprising:

biodegradable particles for delivery of a therapeutic, prophylactic or diagnostic agent, wherein the particles have a tap density less than 0.4 $g/cm^3$, at least approximately 90% of the particles have a mass mean diameter between 5 $\mu$m and 30 $\mu$m, the aerodynamic diameter of the particles is between one and three microns, the particles are suitable for delivery to the deep lung, and a therapeutic, prophylactic or diagnostic agent is incorporated into or adsorbed onto the biodegradable particles.

2. The composition of claim 1 wherein at least 50% of the particles have a mass mean diameter between 5 $\mu$m and 15 $\mu$m.

3. The composition of claim 1 further comprising a pharmaceutically acceptable carrier for administration to the lungs.

4. The composition of claim 1 wherein the particles comprise a functionalized polyester graft copolymer comprising:

a linear $\alpha$-hydroxy-acid polyester backbone having at least one amino acid group incorporated therein; and at least one poly(amino acid) side chain extending from an amino acid group in the polyester backbone.

5. The composition of claim 4 wherein the particles comprise an excipient or a fatty acid.

6. The composition of claim 4 wherein the linear $\alpha$-hydroxy-acid polyester backbone comprises a poly(lactic acid) polymer having at least one lysine group incorporated therein; and wherein the poly(amino acid) extends from at least one lysine group in the polyester backbone.

7. The composition of claim 6 wherein the poly(amino acid) is a polymer of an amino acid selected from the group consisting of aspartic acid, lysine and alanine, and copolymers thereof.

8. The composition of claim 6 wherein the polymer is selected from the group consisting of poly(lactic acid-co-lysine-graft-lysine) and poly(lactic acid-co-lysine-graft-alanine-lysine).

9. The composition of claim 4 wherein the particles comprise a blend of a polyester and the functionalized polyester graft copolymer.

10. The composition of claim 9 wherein the particles comprise a blend of poly(lactic acid-co-lysine-graft-lysine) and poly(lactic acid-co-glycolic acid-block-ethylene oxide).

11. The composition of claim 4 wherein the poly(amino acid) side chain includes about 10–100 amino acids.

12. The composition of claim 4 wherein the polymer has an amino acid content of about 7–70%.

13. The composition of claim 1 wherein the therapeutic agent is selected from the group consisting of proteins, polysaccharides, lipids, nucleic acids and combinations thereof.

14. The composition of claim 1 wherein a targeting molecule is attached to the particle.

15. The composition of claim 1 combined with large biodegradable carrier particles, containing no therapeutic, the mass mean diameter of which is in the range of 50 $\mu$m and 100 $\mu$m.

16. A method for drug delivery to the pulmonary system comprising:

administering to the respiratory tract of a patient in need of treatment an effective amount of biodegradable particles for delivery of a therapeutic, prophylactic or diagnostic agent, wherein the particles have a tap density less than about 0.4 $g/cm^3$, at least approximately 90% of the particles have a mass mean diameter between 5 $\mu$m and 30 $\mu$m, the aerodynamic diameter of the particles is between one and three microns, the particles are deliverable to the deep lung, and a therapeutic agent, prophylactic or diagnostic agent is incorporated into or adsorbed onto the biodegradable particles.

17. The method of claim 16 wherein at least 50% of the administered particles have a mass mean diameter between 5 $\mu$m and 15 $\mu$m.

18. The method of claim 16 wherein the particles comprise a functionalized polyester graft copolymer comprising:

a linear $\alpha$-hydroxy-acid polyester backbone having at least one amino acid group incorporated therein; and at least one poly(amino acid) side chain extending from an amino acid group in the polyester backbone.

19. The method of claim 16 wherein the particles comprise an excipient or a fatty acid.

20. The method of claim 16 wherein the linear $\alpha$-hydroxy-acid polyester backbone comprises a poly(lactic acid) polymer having at least one lysine group incorporated therein; and wherein the poly(amino acid) extends from at least one lysine group in the polyester backbone.

21. The method of claim 16 wherein the polymer is selected from the group consisting of poly(lactic acid-co-lysine-graft-lysine) and poly(lactic acid-co-lysine-graft-alanine-lysine).

22. The method of claim 16 wherein the particles comprise a blend of a polyester and the functionalized polyester graft copolymer.

23. The method of claim 22 wherein the particles comprise a blend of poly(lactic acid-co-lysine-graft-lysine) and poly(lactic acid-co-glycolic acid-block-ethylene oxide).

24. The method of claim 16 wherein the therapeutic agent is selected from the group consisting of proteins, polysaccharides, lipids, nucleic acids and combinations thereof.

25. The method of claim 16 for delivery to the alveolar zone of the lung wherein at least 90% of the particles have a mean diameter between about 9 $\mu$m and 11 $\mu$m.

26. The method of claim 16 wherein the particles are administered in combination with a pharmaceutically acceptable carrier for administration to the respiratory tract.

27. The composition of claim 1 wherein the particles have an irregular surface structure.

28. The method of claim 16 wherein the particles have an irregular surface structure.

* * * * *

UNITED STATES PATENT AND TRADEMARK OFFICE

CERTIFICATE OF CORRECTION

PATENT NO. : 5,874,064 C1
DATED : December 10, 2002
INVENTOR(S) : David A. Edwards et al.

It is certified that error appears in the above-identified patent and that said Letters Patent is hereby corrected as shown below:

Title page,
Item [75], Inventors, "Noah Lotan," delete "Haifa (IL)" and insert -- Haifa Israel --.

Signed and Sealed this

Twenty-seventh Day of May, 2003

JAMES E. ROGAN
*Director of the United States Patent and Trademark Office*

US005874064C1

(12) REEXAMINATION CERTIFICATE (4679th)

United States Patent

Edwards et al.

(10) Number: US 5,874,064 C1

(45) **Certificate Issued: *Dec. 10, 2002**

(54) AERODYNAMICALLY LIGHT PARTICLES FOR PULMONARY DRUG DELIVERY

(75) Inventors: David A. Edwards, State College, PA (US); Giovanni Caponetti, Piacenza (IT); Jeffrey S. Hrkach, Somerville, MA (US); Noah Lotan, Haifa (IL); Justin Hanes, Baltimore, MD (US); Abdell Aziz Ben-Jebria, State College, PA (US); Robert S. Langer, Newton, MA (US)

(73) Assignees: Massachusetts Institute of Technology, Cambridge, MA (US); The Penn State Research Foundation, University Park, PA (US)

Reexamination Request:
No. 90/006,092, Aug. 22, 2001

Reexamination Certificate for:

| | |
|---|---|
| Patent No.: | **5,874,064** |
| Issued: | **Feb. 23, 1999** |
| Appl. No.: | **08/739,308** |
| Filed: | **Oct. 29, 1996** |

(*) Notice: This patent is subject to a terminal disclaimer. 08/739,308

Related U.S. Application Data

(63) Continuation-in-part of application No. 08/655,570, filed on May 24, 1996.

(51) Int. Cl.[7] ........................ A61K 9/12

(52) U.S. Cl. .................. 424/46; 424/43; 424/489; 424/491; 424/426; 424/434; 424/45

(58) Field of Search .................. 424/46, 43, 489, 424/491, 426, 434

(56) References Cited

U.S. PATENT DOCUMENTS

| | | | |
|---|---|---|---|
| 5,458,135 A | 10/1995 | Patton et al. | 128/200.14 |
| 5,780,014 A | 7/1998 | Eljamal et al. | 424/46 |
| 5,795,594 A | 8/1998 | York et al. | 424/489 |
| 5,851,453 A | 12/1998 | Hanna et al. | 264/5 |
| 6,063,138 A | 5/2000 | Hanna et al. | 23/295 |

FOREIGN PATENT DOCUMENTS

| | | |
|---|---|---|
| WO | WO 95/01221 | 1/1995 |
| WO | WO 95/01324 | 1/1995 |
| WO | WO 96/00610 | 1/1996 |

OTHER PUBLICATIONS

File History for U.S. patent application Ser. No. 08/423,515, filed Apr. 14, 1995, to Platz et al.

Gonda, I. "Physico–chemical principles in aerosol delivery," in *Topics of Pharmaceutical Sciences* 1991 (eds. D.J.A. Crommelin and K.K. Midha).

*Primary Examiner*—Mina Haghighatian

(57) ABSTRACT

Improved aerodynamically light particles for drug delivery to the pulmonary system, and methods for their synthesis and administration are provided. In a preferred embodiment, the aerodynamically light particles are made of a biodegradable material and have a tap density less than 0.4 $g/cm^3$ and a mass mean diameter between 5 $\mu m$ and 30 $\mu m$. The particles may be formed of biodegradable materials such as biodegradable polymers. For example, the particles may be formol of a functionalized polyester graft copolymer consisting of a linear α-hydroxy-acid polyester backbone having at least one amino acid group incorporated therein and at least one poly(amino acid) side chain extending from an amino acid group in the polyester backbone. In one embodiment, aerodynamically light particles having a large mean diameter, for example greater than 5 $\mu m$, can be used for enhanced delivery of a therapeutic agent to the alveolar region of the lung. The aerodynamically light particles incorporating a therapeutic agent may be effectively aerosolized for administration to the respiratory tract to permit systemic or local delivery of wide variety of therapeutic agents.

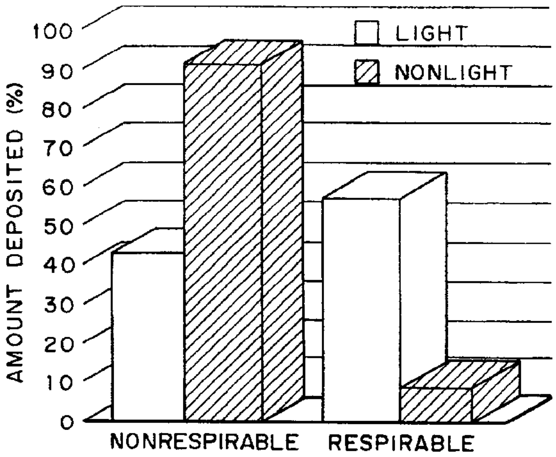

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–28 is confirmed.

* * * * *